United States Patent [19]

Furukawa

[11] Patent Number: 4,989,586
[45] Date of Patent: Feb. 5, 1991

[54] ENDOSCOPE HAVING A SOLID-STATE IMAGE PICKUP DEVICE

[75] Inventor: Tatsuya Furukawa, Hachioji, Japan

[73] Assignee: Olympus Optical Co., Ltd., Tokyo, Japan

[21] Appl. No.: 520,278

[22] Filed: May 7, 1990

[30] Foreign Application Priority Data

Jul. 21, 1989 [JP] Japan .................. 1-85785[U]

[51] Int. Cl.⁵ .............................................. A61B 1/04
[52] U.S. Cl. .................................... 128/6; 358/98
[58] Field of Search ................... 128/4, 6; 358/98

[56] References Cited

U.S. PATENT DOCUMENTS

| | | | |
|---|---|---|---|
| 4,677,471 | 6/1987 | Takamura et al. | 358/98 |
| 4,831,456 | 5/1989 | Takamura | 358/98 X |
| 4,841,949 | 6/1989 | Shimizu et al. | 128/4 |
| 4,919,114 | 4/1990 | Miyazaki | 128/6 |

FOREIGN PATENT DOCUMENTS

| | | |
|---|---|---|
| 62-90602 | 6/1987 | Japan . |
| 63-96801 | 6/1988 | Japan . |
| 64-31705 | 2/1989 | Japan . |

*Primary Examiner*—William H. Grieb

[57] ABSTRACT

An endoscope having a solid-state image pickup device in the distal end of the insert portion of the endoscope, the central axis of the solid-state image pickup device being apart from the central axis of the insert portion. Signal lines connected to the solid-state image pickup device are directed slantingly from the solid-state image pickup device toward the central axis of the insert portion of the endoscope. Thus, the diameter of the bending portion can be reduced without the interference of the signal lines with members contained in the peripheral area of the bending portion of the endoscope.

13 Claims, 8 Drawing Sheets

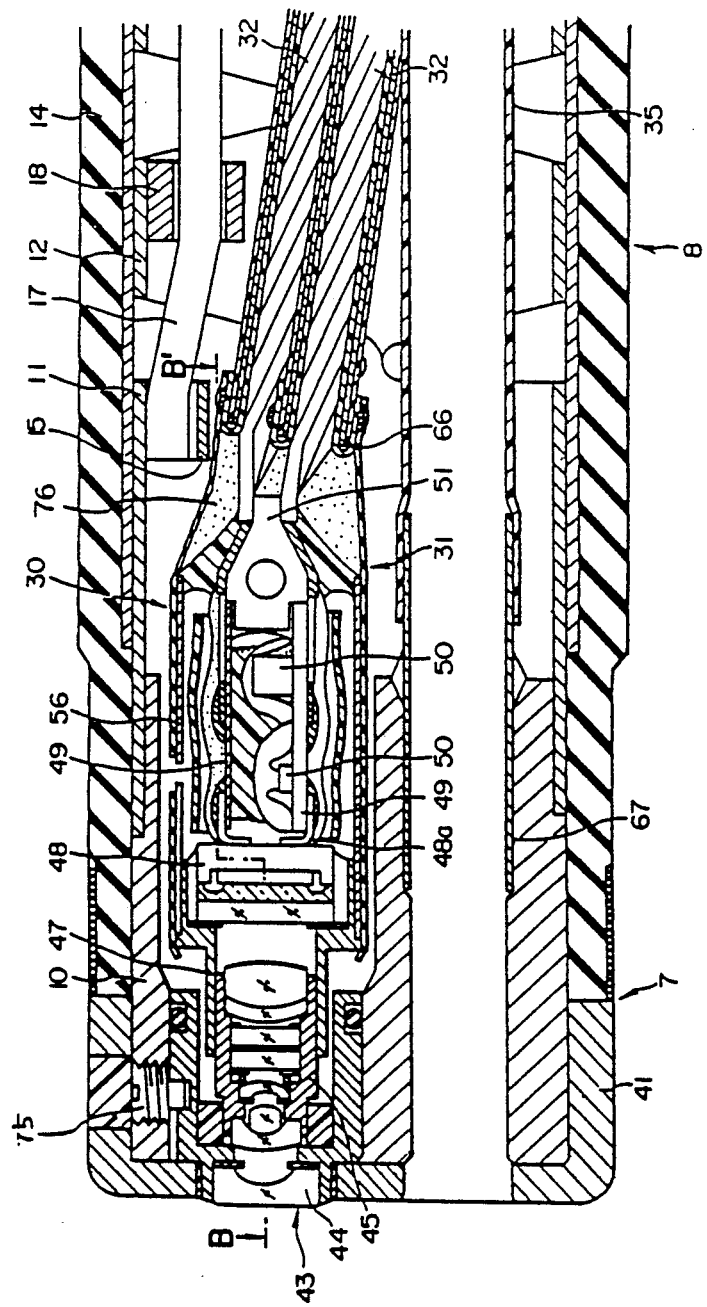
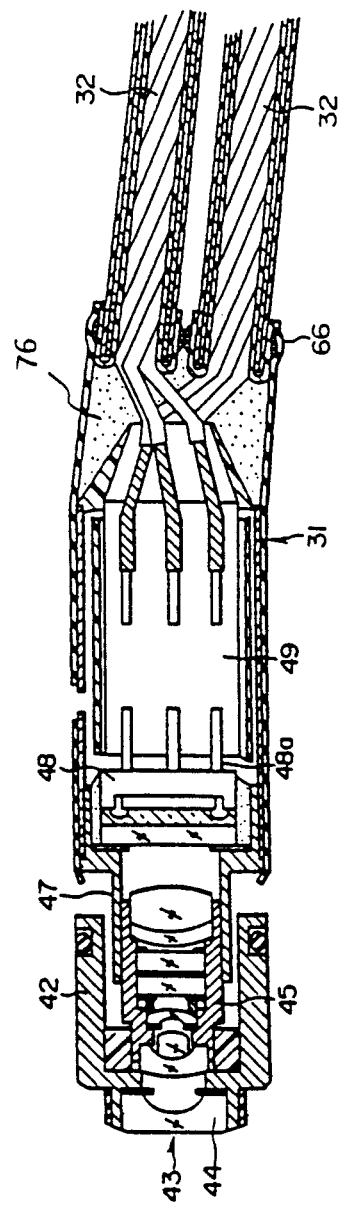
FIG. 5
FIG. 6

ENDOSCOPE HAVING A SOLID-STATE IMAGE PICKUP DEVICE

BACKGROUND OF THE INVENTION

1. Field of the Invention

This invention relates to an endoscope having a solid-state image pickup device in its distal end portion.

2. Description of Related Art

In recent years, wide use has been made of endoscopes which have elongated insert portions to be inserted into body cavities to observe internal organs, and treating instrument channels into which treating instruments are inserted to perform various treating operations. Also use has been made of electronic endoscopes which have solid-state image pickup devices, such as CCDs, in the distal end portions of the insert portions.

As shown in FIG. 1, an electronic endoscope is provided in the distal end portion 7 of the insert portion with an image pickup portion 30 comprising an objective optical system 43 and an image pickup unit including a solid-state image pickup device 48 and its peripheral circuitry. Conventionally, signal lines 32 connected to the image pickup unit of the solid-state image pickup portion 30 have been arranged in the peripheral area of the distal end portion 7 from a standpoint of layout and extended from the rear end of the image pickup portion 30 into a bending portion 8 vertically, that is, in parallel with the axis of the insert portion.

However, the bending portion 8 of the insert portion includes in its peripheral area a wire 17 for bending operation, a wire guide 15 for fixing the distal end of the wire 17, and a wire receiver 18 through which the wire 17 extends. Since the signal lines 32 have long rigid portions extended from the rear end of the image pickup portion 30, there is a fear that the wire guide 15, the wire receiver 18, the wire 17, etc., will interfere with the signal lines 32 when the bending portion 8 is bent. This interference may break the signal lines 32 or affect the bending operation 8.

Therefore, conventionally the bending portion 8 has had to be thick in order to prevent the wire guide 15, the wire receiver 18, the wire 17, etc., from interfering with the signal lines 32.

SUMMARY OF THE INVENTION

An object of the present invention is to provide an endoscope in which the diameter of the bending portion can be reduced without affecting the durability of the signal lines.

The object of the invention can be attained by an endoscope comprising a solid-state image pickup device arranged in the distal end portion of an insert portion, the central axis of the solid-state image pickup device being apart from the central axis of the insert portion; a plurality of signal lines arranged in the insert portion for transmitting a drive signal to the solid-state image pickup device and an image signal from the solid-state image pickup device; and holding means provided in the connecting portion of the signal lines with the solid-state image pickup device for holding the signal lines in such a manner that the signal lines are fixed in a slanting state with respect to the central axis of the insert portion and directed from the solid-state image pickup device toward the central axis of the insert portion.

Since the signal lines are directed toward the central axis of the insert portion, the diameter of the insert portion can be reduced without any interference with the wire guide, wire receiver, wire, etc.

BRIEF DESCRIPTION OF THE DRAWINGS

FIG. 5 is a sectional view of a distal end portion of an insert portion of an endoscope according to a second embodiment of the present invention.

FIG. 6 is a sectional view along line B-B' of FIG. 5.

DESCRIPTION OF THE PREFERRED EMBODIMENTS

Figure 1:
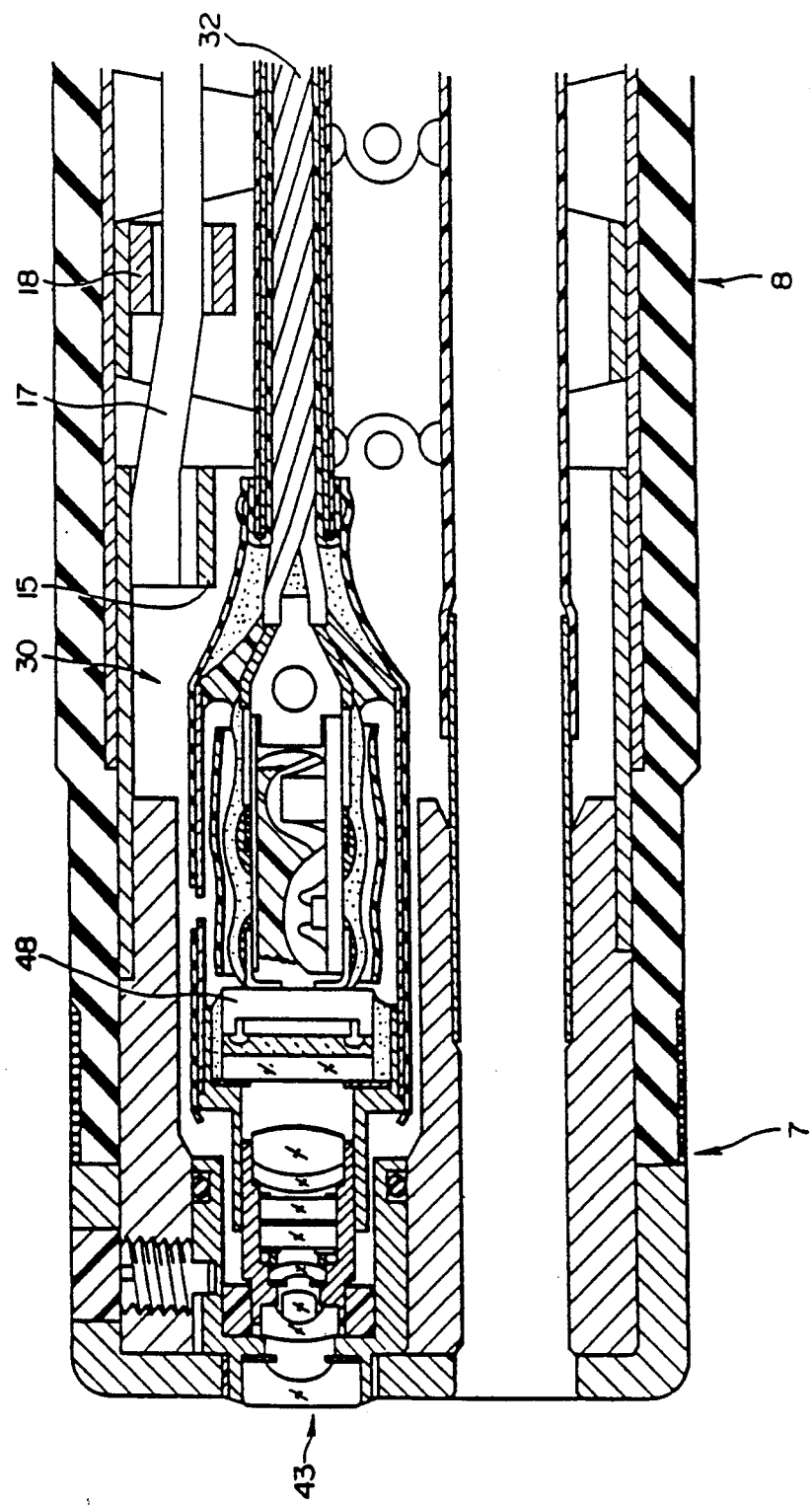
FIG. 1 is a sectional view of a distal end portion of an insert portion of a conventional endoscope.
Figure 2:
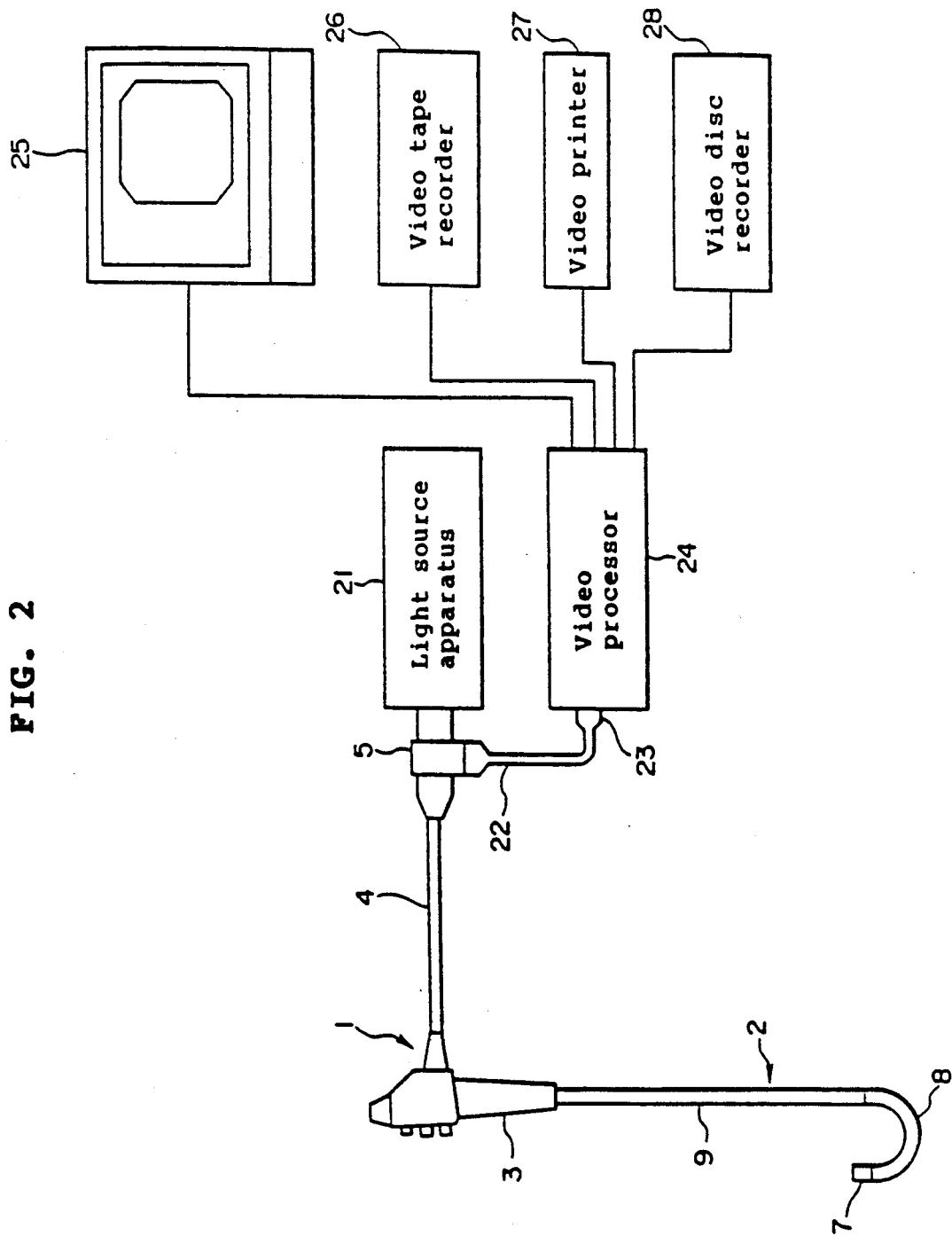
FIG. 2 is a diagram showing an endoscope system.
Figure 3:
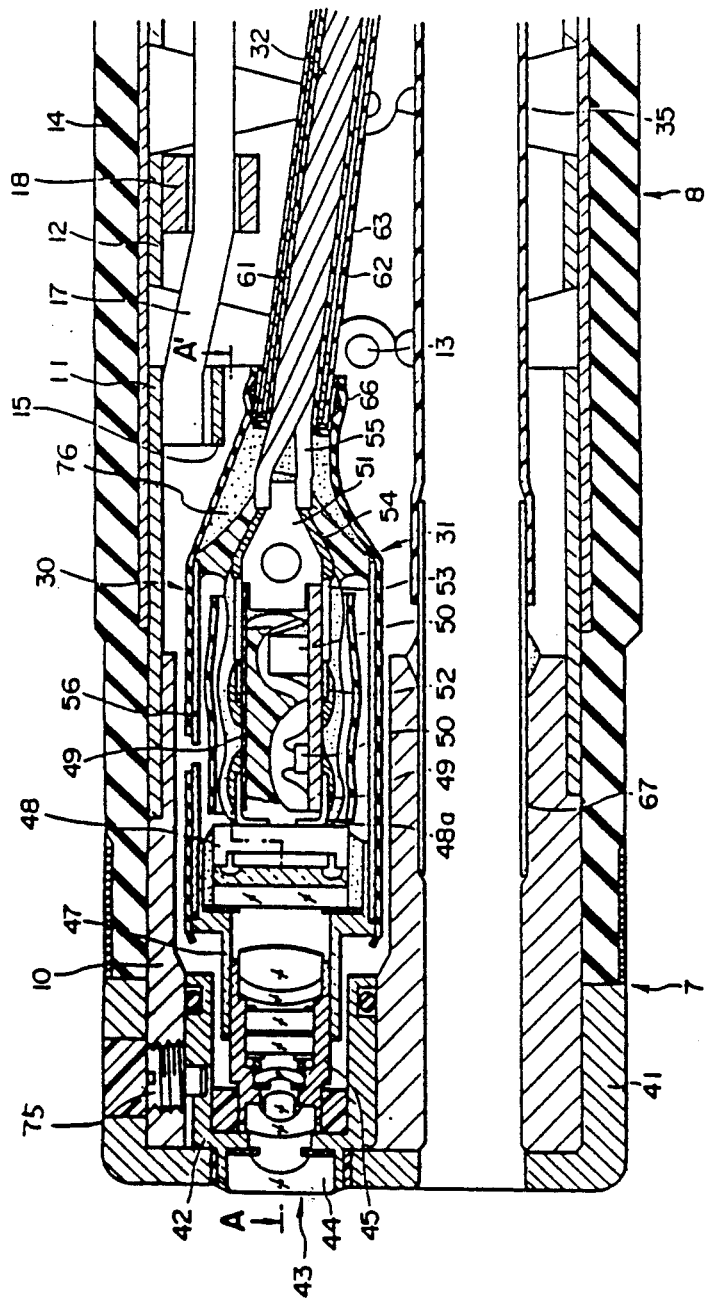
FIG. 3 is a sectional view of a distal end portion of an insert portion of an endoscope according to a first embodiment of the present invention.
Figure 4:
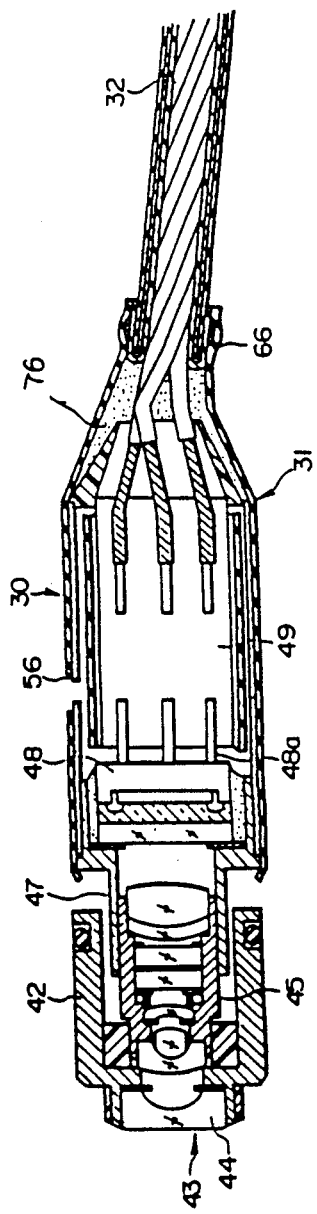
FIG. 4 is a sectional view along line A-A' of FIG. 3.

Referring to FIGS. 2 to 4, a first embodiment of the present invention will be described.

FIG. 2 is a diagram showing an endoscope system. FIG. 3 is a sectional view of a distal end portion of an insert portion of an endoscope. FIG. 4 is a cross-sectional view along line A-A' of FIG. 3. In FIG. 4, members 61, 62 and 63 covering signal lines 32 are also represented as sectional.

As shown in FIG. 2, an endoscope 1 has an elongated flexible insert portion 2 and a thick operating portion 3 connected to the proximal end of the insert portion 2. A universal cord 4 extends laterally from the operating portion 3 to a connector 5, which is connected to a light source apparatus 21. A signal cord 22 extends from the connector 5 to a connector 23, which is connected to a video processor 24. The video processor 24 is connected to a monitor 25, a video tape recorder 26, a video printer 27, a video disc recorder 28, etc. The insert portion 2 comprises a rigid distal end portion 7, a bending portion 8, and a flexible tube 9 in this order.

As shown in FIG. 3, the distal end portion 7 has a distal end member 10, to which an end cover 41 is attached. The distal end member 10 and the end cover 41 are provided with an illuminating window, a viewing window, an opening for supplying air and water, and a forceps channel opening.

An illuminating lens (not shown) is mounted inside the illuminating window. At the rear end of the illuminating lens, a light guide (not shown) composed of a fiber bundle is arranged. The light guide passes through the insert portion 2, the operating portion 3 and the universal cord 4 and is connected to the connector 5. Illuminating light emitted from a lamp of the light source apparatus 21 impinges on the light entering surface of the light guide.

Inside the viewing window, an image pickup portion 30 having an objective optical system 43 and a solid-state image pickup device assembly 31 is provided. The solid-state image pickup device assembly 31 has a solid-state image pickup device 48 arranged at the image plane of the objective optical system 43. Signal lines 32 connected to the solid-state image pickup device 48 via a substrate 49 pass through the insert portion 2, the operating portion 3, the universal cord 4, the connector 5 and the signal cord 22 and is connected to the connector 23, which is connected to the video processor. The solid-state image pickup device 48 is driven by the video processor 24, and the output signal of the solid-state image pickup device 48 undergoes the image signal processing by the video processor 24. The image signal from the video processor 24 is inputted to the monitor 25, the video tape recorder 26, the video printer 27, the video disc recorder 28, etc.

The opening for supplying air and water is connected to an air/water supply tube (not shown). The air/water supply tube passes through the insert portion 2, the operating portion 3 and the universal cord 4 and is connected to the connector 5. The forceps channel opening is connected to a forceps channel tube 35 via a channel connecting pipe 67. The forceps channel tube 35 passes through the insert portion 2 and is connected to a forceps insert opening (not shown) provided in the operating portion 3.

The bending portion 8 has a bending tube formed by a large number of quasi-cylindrical articulation members 11 and 12 pivotally connected by articulation axes 13, and the outer periphery of the bending tube is covered by bending rubber 14. The rear end of the most proximal articulation member is connected to the flexible tube 9.

A number of (for example, four) angle wires 17 for bending operation pass through the insert portion 2, and the distal ends of the angle wires are fixed to the most distal articulation member (hereinafter called "the first articulation member") 11 by wire guides 15. The second articulation member 12 and further articulation members behind the second articulation member 12 are provided on their inner periphery with wire receivers 18 at regular intervals, and the angle wires 17 pass through the wire receivers 18. The angle wires 17 are pushed and pulled by an angle operating knob provided in the operating portion 3 thereby bending the bending portion 8 upward and downward or right and left.

Next, the image pickup portion 30 is described in detail.

At the viewing window formed in the distal end member 10 and the end cover 42, a first lens frame 42 is secured by an screw 75. A front lens 44 of the objective optical system 43 is mounted in the first lens frame 42. Inside the first lens frame 42, a second lens frame 45 is fixed, and the other lenses of the objective optical system 43 are mounted in the second lens frame 45. The rear end portion of the second lens frame 45 is connected to the solid-state image pickup device assembly 31. The solid-state image pickup assembly 31 is constructed in the following manner: The rear end portion of the second lens frame 45 is connected to a device frame 47, to which the solid-state image pickup device 48 such as a CCD is fixed. Leads 48a of the solid-state image pickup device 48 is connected to the substrate 49 on which electronic elements 50 are mounted. The substrate 49 is connected to the signal lines 32 via a cable fixing member 51. The signal lines 32 are coaxial cables; the cable cores 52 are connected to the substrate 49, and shielding lines 54 are electrically connected by a conductive adhesive agent to a shielding member 56 which covers the solid-state image pickup device 48 and the substrate 49. The cable cores 52 and the shielding lines 54 are covered by insulating tubes 53 and cover tubes 55, respectively.

The cables 32 are covered by a holding tape 61, an overall shield 62 and an overall cover tube 63 in this order. The outer periphery of the shielding member 56 and the connecting portion of the cables 32 are covered by a thermocontractive tube 66. An adhesive agent 76 is filled in the space between the thermocontractive tube 66 and the cable fixing member 51. When the adhesive agent 76 becomes hard, it forms a inflexible portion near the distal end of the signal lines 32.

As shown in FIG. 3, the image pickup portion 30 is arranged in the peripheral area of the distal end portion 7.

In this embodiment, as shown in FIGS. 3 and 4, the signal lines 32 extend from the rear end of the image pickup portion 30 slantingly toward the central axis of the insert portion 2 in order to avoid the interference with the wire guide 15 of the first articulation 11 and the wire receiver 18 of the second articulation 12. The slantingly extending state is maintained by the adhesive agent 76. Hence, it is not necessary to thicken the bending portion 8 so as to prevent the wire guide 15 and the wire receiver 18 from interfering with the signal lines 32. Thus, it is possible to reduce the diameter of the bending portion 8 without affecting the durability of the signal lines 32 and to relieve patients of pain during endoscopic examination.

Next, referring to FIGS. 5 to 8, a second embodiment of the present invention will be described.

Figure 7:
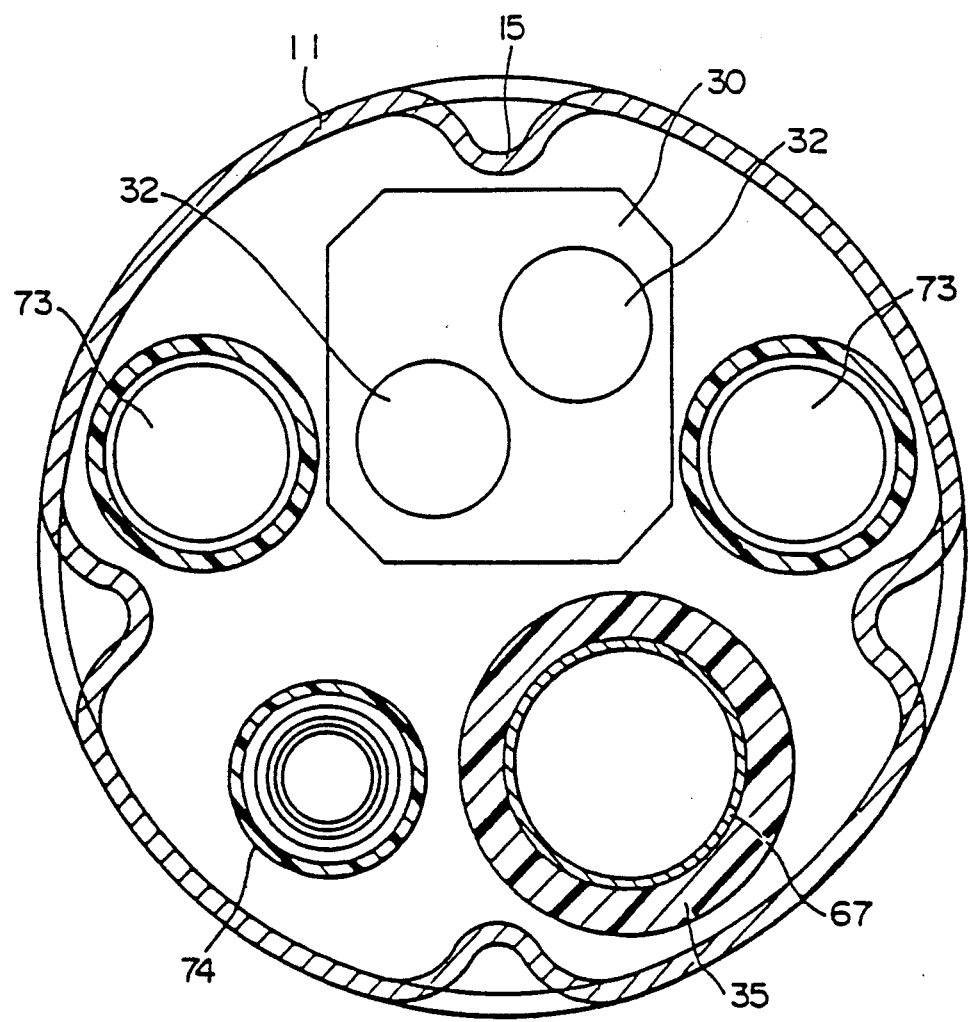
FIG. 7 is a cross-sectional view showing the arrangement of elements in the first articulation of the insert portion according to the second embodiment.
Figure 8:
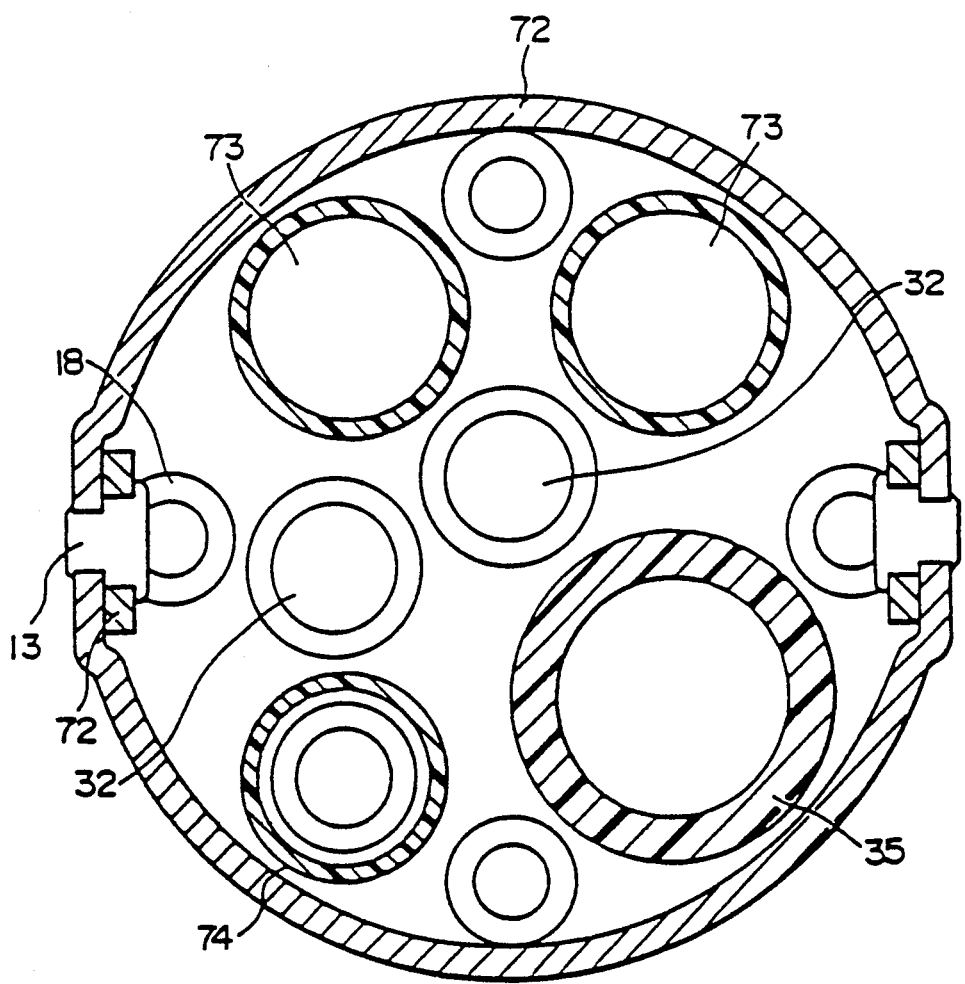
FIG. 8 is a cross-sectional view showing the arrangement of elements in a bending portion of the endoscope according to the second embodiment.

FIG. 5 is a sectional view of a distal end portion of an insert portion of an endoscope. FIG. 6 is a sectional view along line B-B' of FIG. 5. FIG. 7 is a cross-sectional view showing the arrangement of elements in the first articulation of the insert portion. FIG. 8 is a cross-sectional view showing the arrangement of elements in a bending portion. In FIG. 6, members covering signal lines 32 are also represented as sectional.

In this embodiment, as shown in FIGS. 5 and 6, signal lines 32 are divided into a plurality of (for example, two) groups. In the same way as in the first embodiment, the two groups of signal lines 32, 32 extend from the rear end of an image pickup portion 30 slantingly toward the central axis of the insert portion 2 to avoid the interference with a wire guide 15 of the first articulation 11 and a wire receiver 18 of the second articulation 12. An adhesive agent 76 is filled in the space between a thermocontractive tube 66 and a cable fixing member 51 to maintaining the slantingly extending state of the signal lines 32.

As shown in FIG. 7, among the other elements contained in the insert portion 2, two light guides 73, 73 are positioned on both sides of the image pickup portion 30 in the first articulation 11. As shown in FIG. 8, however, in the second articulation 12 and further articulations behind the second articulation 12, the light guides 73, 73 are located in the upper space of FIG. 8 since the image pickup portion 30 does not exist here and the signal lines 32, 32 are arranged in the vicinity of the central axis of the insert portion 2.

An air/water supply tube 74 and a forceps channel tube 35 are arranged in the lower portion both in the first articulation 11 and in the second articulation 12 and further articulations.

In FIG. 8, numerals 72, 72 denote articulation members coupled together by an articulation axis 13.

Other structure, operation and effect of this embodiment are the same as those of the first embodiment.

Figure 9:
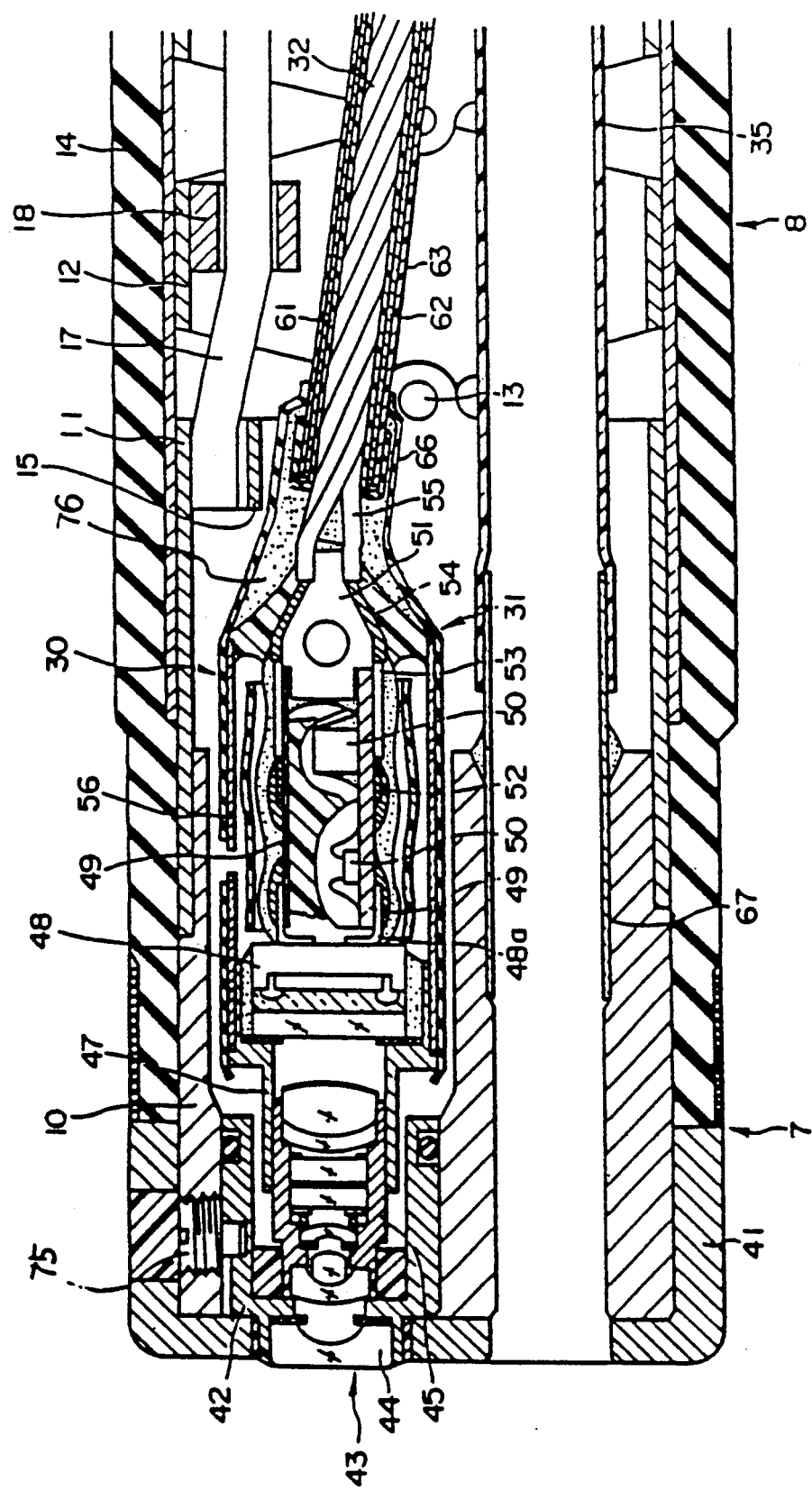
FIG. 9 is a sectional view of a distal end portion of an insert portion of an endoscope according to a third embodiment of the present invention.

FIG. 9 shows a third embodiment of the present invention.

Also in this embodiment, signal lines 32 extend from the rear end of an image pickup portion 30 slantingly toward the central axis of the insert portion 2. The outer periphery of the signal lines 32 are covered by a holding tape 61, an overall shield 62 and an overall cover tube 63 in this order. The distal end of the holding tape 61 is folded back to cover a part of the outer periphery of the overall cover tube 63. An insulating thermocontractive tube 66 covering a shield member 56 extends backward beyond the folded-back part of the holding tape 61 and is fixed to the outer surface of the overall cover tube 63 with an adhesive agent 76 filled therein. The adhesive agent 76 maintains the slantingly extending state of the signal lines 32. That part of the signal lines 32 which is covered by the thermocontractive tube 66 is inflexible owing to the adhesive agent 76 so that the signal lines 32 do not interfere with a wire guide 15 and a wire receiver 18.

Figure 10:
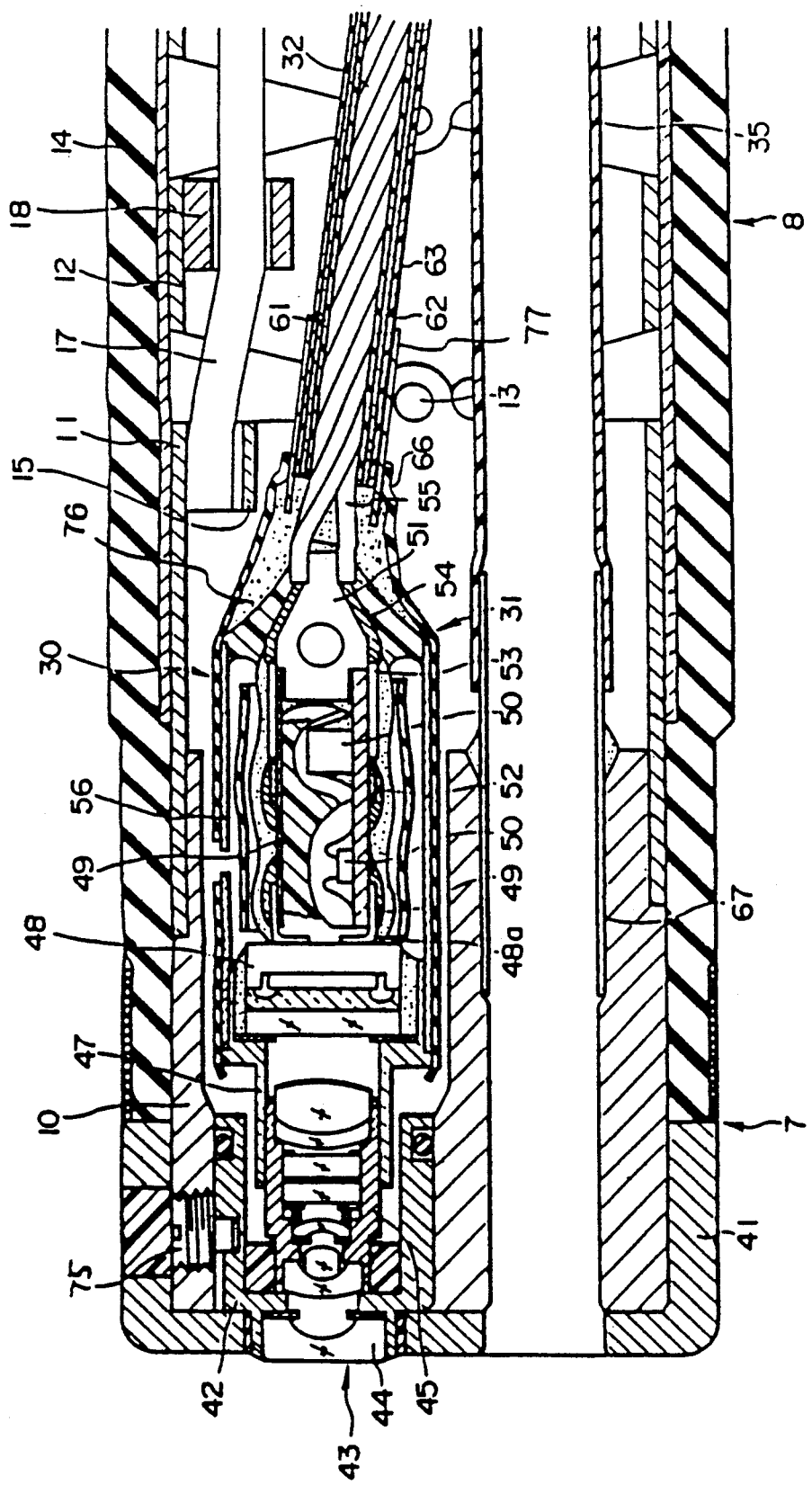
FIG. 10 is a sectional view of a distal end portion of an insert portion of an endoscope according to a fourth embodiment of the present invention.

FIG. 10 shows a fourth embodiment of the present invention.

Compared with the first embodiment, this embodiment further comprises a rigid pipe 77 between a thermocontractive tube 66 and signal lines 32. The pipe 77 is secured to the outer surface of an overall cover tube 63 of the signal lines 32, and the thermocontractive tube 66 is fixed to the distal outer periphery of the pipe 77 via an adhesive agent 76. Thus, the signal lines 32 are rigid due to the adhesive agent 76 in the vicinity of the rear end of an image pickup portion 30 and due to the pipe 77 behind it so that the slantingly extending state of the signal lines 32 from the image pickup portion 30 is maintained. This embodiment makes it possible to lengthen the inflexible distal part of the signal lines 32 so that the signal lines 32 can be more effectively directed toward the central axis of the insert portion 2.

What is claimed is:

1. An endoscope comprising:
    an insert portion having a distal end portion and a central axis;
    a solid-state image pickup device arranged in the distal end portion of the insert portion and having a central axis, the central axis of the solid-state image pickup device being apart from the central axis of the insert portion;
    a plurality of signal lines arranged in the insert portion and connected to the solid-state image pickup device for transmitting a drive signal to the solid-state image pickup device and an image signal from the solid-state image pickup device; and
    holding means provided in the connecting portion of the signal lines with the solid-state image pickup device for holding the signal lines in such a manner that the signal lines are fixed in a slanting state with respect to the central axis of the insert portion and directed from the solid-state image pickup device toward the central axis of the insert portion.

2. The endoscope of claim 1, in which the holding means includes an adhesive agent which covers the connecting portion of the signal lines with the solid-state image pickup device and fixes the connecting portion in the slanting state.

3. The endoscope of claim 1, in which the signal lines are grouped into at least one group covered by a cover tube; the solid-state image pickup device is covered by an insulating tube; and the distal end of the cover tube is inserted into and fixed to the proximal end of the insulating tube.

4. The endoscope of claim 3, in which a space behind the solid-state image pickup device is defined by the insulating tube, and an adhesive agent is filled into the space to form the holding means.

5. The endoscope of claim 3, in which the insulating tube covering the solid-state image pickup device is thermocontractive.

6. The endoscope of claim 3, in which the cover tube and the insulating tube are fixed together via an annular member.

7. An endoscope comprising:
    an insert portion including a distal end portion, a bending portion, a proximal end portion, and a central axis; the distal end portion having an objective lens; and the bending portion being formed by a plurality of articulations with a wire connected to the articulations, the bending portion being bendable by pulling the wire;
    a wire securing member provided in the bending portion for securing the wire;
    solid-state image pickup means for receiving a light image from the objective lens, at least a part of the solid-state image pickup means being positioned in front of the wire securing member;
    an electric cord connected to the solid-state image pickup means and led to the proximal end portion of the insert portion; and
    an adhesive agent applied to the connecting portion of the electric cord with the solid-state image pickup means for maintaining the electric cord to guide the electric cord in a direction toward the central axis of the insert portion as far as a position where the electric cord does not interfere with the wire securing member.

8. The endoscope of claim 7, in which the adhesive agent is covered by a cover member which covers the solid-state image pickup means.

9. The endoscope of claim 7, in which the electric cord is covered by a rigid pipe member in the vicinity of the distal end of the electric cord, and the pipe member is fixed with respect to the solid-state image pickup device by the adhesive agent in a slanting direction toward the central axis of the insert portion, thereby aiding the positional control of the electric cord by the adhesive agent.

10. An endoscope comprising:
    an insert portion having a distal end portion and a central axis;
    a solid-state image pickup device arranged in the distal end portion and having a central axis, the central axis of the solid-state image pickup device being apart from the central axis of the insert portion;
    an electric cord arranged in the insert portion and having an inflexible portion in the vicinity of the distal end of the electric cord, the electric cord including flexible signal lines for transmitting a drive signal to the solid-state image pickup device and an image signal from the solid-state image pickup device; and
    fixing means for fixing the inflexible portion of the electric cord with respect to the solid-state image pickup device in a slanting direction toward the central axis of the insert portion to guide the electric cord toward the central axis.

11. The endoscope of claim 10, in which the inflexible portion of the electric cord is formed by applying a layer of an adhesive agent on the electric cord.

12. The endoscope of claim 10, in which the inflexible portion of the electric cord is formed by covering the electric cord with a rigid pipe.

13. The endoscope of claim 10, in which the fixing means is an adhesive agent applied on the solid-state image pickup device and the electric cord.

* * * * *